(12) United States Patent
Buechi

(10) Patent No.: US 10,245,398 B2
(45) Date of Patent: Apr. 2, 2019

(54) RESPIRATORY HUMIDIFIER AND LIGHTING DEVICE FOR RESPIRATORY HUMIDIFIER

(71) Applicant: Hamilton Bonaduz AG, Bonaduz (CH)

(72) Inventor: Rudolf Buechi, Chur (CH)

(73) Assignee: Hamilton Medical AG (CH)

( * ) Notice: Subject to any disclaimer, the term of this patent is extended or adjusted under 35 U.S.C. 154(b) by 647 days.

(21) Appl. No.: 14/348,974

(22) PCT Filed: Sep. 27, 2012

(86) PCT No.: PCT/EP2012/069128
§ 371 (c)(1),
(2) Date: Apr. 1, 2014

(87) PCT Pub. No.: WO2013/045578
PCT Pub. Date: Apr. 4, 2013

(65) Prior Publication Data
US 2014/0299126 A1 Oct. 9, 2014

(30) Foreign Application Priority Data
Oct. 1, 2011 (DE) .................. 10 2011 054 135

(51) Int. Cl.
| | |
|---|---|
| *A61M 16/00* | (2006.01) |
| *A61M 16/16* | (2006.01) |
| *F21V 33/00* | (2006.01) |
| *A61M 16/10* | (2006.01) |

(52) U.S. Cl.
CPC ...... *A61M 16/0051* (2013.01); *A61M 16/109* (2014.02); *A61M 16/1075* (2013.01);
(Continued)

(58) Field of Classification Search
CPC .............. A61M 16/16; A61M 16/1075; A61M 2205/18; A61M 2205/3368;
(Continued)

(56) References Cited

U.S. PATENT DOCUMENTS

| | | | | |
|---|---|---|---|---|
| 4,098,853 A | * | 7/1978 | Brown | A61M 16/1075 128/200.13 |
| 4,622,976 A | | 11/1986 | Timpe et al. | |

(Continued)

FOREIGN PATENT DOCUMENTS

| | | |
|---|---|---|
| DE | 2525455 A1 | 6/1975 |
| DE | 202007004247 U1 | 3/2007 |
| WO | WO 2010031126 A1 * 3/2010 | ........ A61M 16/0816 |

*Primary Examiner* — Gregory Anderson
*Assistant Examiner* — Elliot S Ruddie
(74) *Attorney, Agent, or Firm* — Jansson Munger McKinley & Kirby Ltd.

(57) ABSTRACT

A lighting device for a respiratory humidifier (1) is provided, the humidifier comprising a liquid container (3) with a bottom plate and a housing (2) with a heating plate (8), wherein the heating plate (8) can be heated for heating the liquid in the liquid container (3), and wherein the bottom plate can be brought into contact with the heating plate (8), wherein the housing (2) comprises a light source (20) and a light exit portion (22), and the liquid container (3) comprises a light entrance portion (21), wherein the light proceeding from the light source (20) proceeds in a lighting direction through the light exit portion (22) and the light entrance portion (21) and thus arrives in the liquid container (3).

16 Claims, 3 Drawing Sheets

(52) U.S. Cl.
CPC ......... *A61M 16/16* (2013.01); *F21V 33/0068* (2013.01); *A61M 2205/18* (2013.01); *A61M 2205/3368* (2013.01); *A61M 2205/3389* (2013.01); *A61M 2205/502* (2013.01); *A61M 2205/581* (2013.01); *A61M 2205/583* (2013.01); *A61M 2205/587* (2013.01)

(58) Field of Classification Search
CPC .... A61M 2205/3389; A61M 2205/502; A61M 2205/581; A61M 2205/583; A61M 2205/587; A61M 16/109; A61M 16/0051; A61M 16/00; A61M 2205/80; A61B 6/507; F21V 33/0068
USPC ...................................... 128/202.22; 362/101
See application file for complete search history.

(56) References Cited

U.S. PATENT DOCUMENTS

| | | | |
|---|---|---|---|
| 7,753,545 B2 * | 7/2010 | Groover | F21V 23/04 116/227 |
| RE44,453 E * | 8/2013 | Virr | A61M 16/16 128/203.26 |
| 9,067,036 B2 * | 6/2015 | Korneff | A61M 16/0875 |
| 2003/0169588 A1 * | 9/2003 | Kohn | F21V 33/0088 362/101 |
| 2005/0235993 A1 | 10/2005 | Baecke et al. | |
| 2008/0074864 A1 * | 3/2008 | Molders | F24F 6/12 362/101 |
| 2011/0006331 A1 * | 1/2011 | Shaikevitch | H01L 33/507 257/98 |

* cited by examiner

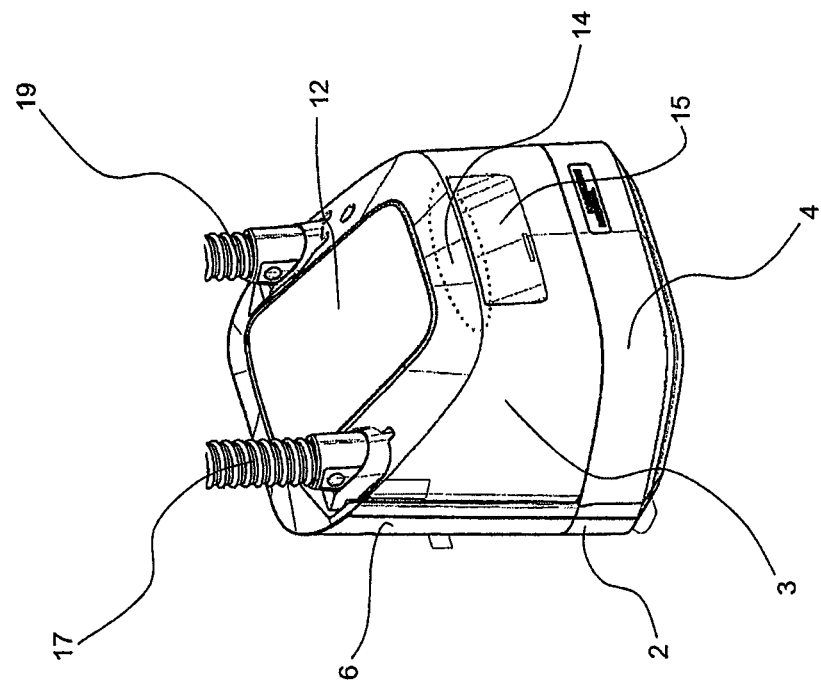
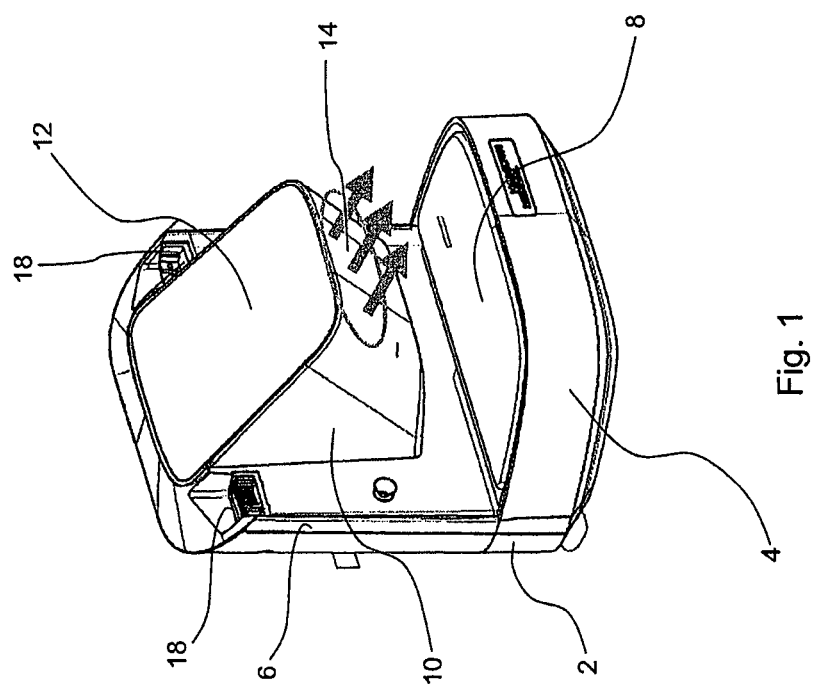

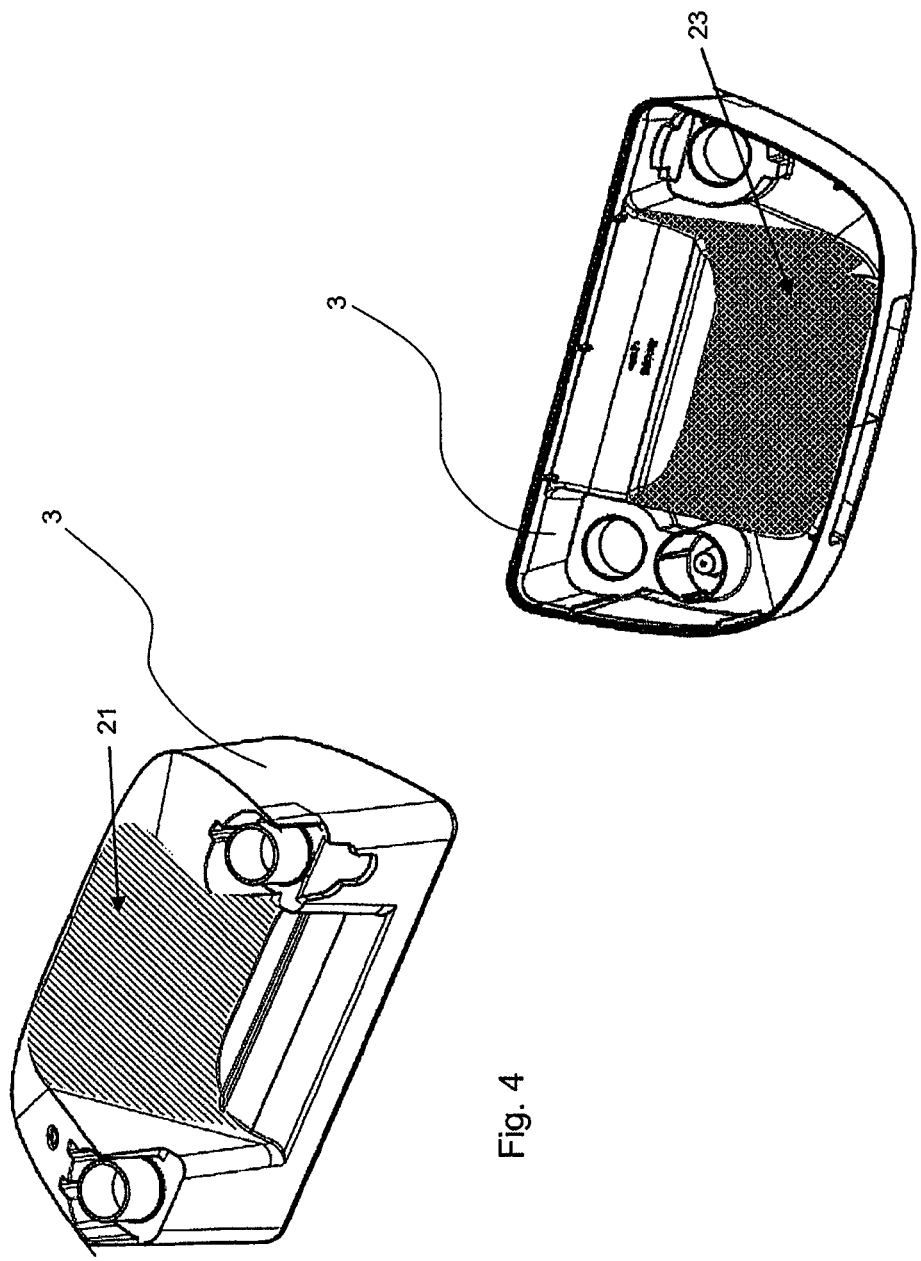

RESPIRATORY HUMIDIFIER AND LIGHTING DEVICE FOR RESPIRATORY HUMIDIFIER

FIELD OF THE INVENTION

The present invention pertains to a lighting device for a respiratory humidifier for ventilating patients with breathing gas.

BACKGROUND OF THE INVENTION

When patients are being mechanically ventilated on an intensive-care ward, for example, the patient to be ventilated is connected pneumatically to the ventilator or respiratory apparatus by a system of ventilation tubing. Because the breathing gas delivered to the patient must be adjusted with respect to temperature and humidity to meet the physiological needs of the patient, a respiratory humidifier is arranged in the inhalation or inspiration tube to heat and humidify the breathing gas. The respiratory humidifier comprises a liquid container filled with distilled water, through which the inhalation or inspiration gas is conducted and humidified.

The heating of the liquid in the liquid container is usually accomplished by means of a heating plate in the bottom part of the housing of the respiratory humidifier, wherein the heat is transferred from the heating plate to the thermally conductive bottom of the liquid container. The temperature of the breathing gas is measured by suitable sensors as it flows in and out, for example.

To avoid the liquid container running dry, the level of the liquid in the container is monitored. If the level falls below a minimum value, liquid from an external reservoir is supplied by way of a float valve, for example. No signal is given to the user to draw his attention to the need to add more liquid and possibly to replace the reservoir.

It is also known that respiratory humidifiers can be equipped with user interfaces, which comprise display elements and operating elements. A control unit regulates or automatically controls the function of the respiratory humidifier and if necessary emits an optical or acoustic signal when a functional state meriting an alarm is present. Because of the small dimensions of the control unit, there is only a limited capacity to provide a clear, optically recognizable signal, e.g., a signal generated by small LEDs forming the display elements.

Another requirement on a respiratory humidifier is that, because the liquid container is a medical-grade, single-use/disposable article, it must be possible to manufacture it especially easily and inexpensively. A design or structure for providing illumination, therefore, should not be too complicated, should comprise the smallest possible number of components, and be manufacturable at reasonable cost.

It is therefore the object of the present invention to provide a lighting device for a respiratory humidifier which can signal the presence of an alarm state in very clear optical fashion in as many directions as possible and which can be realized inexpensively on the basis of a simple design.

This object is achieved by the features of claim 1. Advantageous elaborations and embodiments are described in the subclaims.

SUMMARY OF THE INVENTION

According to an aspect of the invention, a lighting device for a respiratory humidifier is provided, the humidifier comprising a liquid container with a bottom plate and a housing with heating plate, wherein, to heat the liquid in the liquid container, the heating plate can be heated and the bottom plate brought into contact with the heating plate, wherein the housing comprises a light source or light producing means and a light exit portion, wherein the liquid container comprises a light entrance portion, wherein the light proceeding from the light source in a lighting direction passes through the light exit portion and the light entrance portion and thus arrives in the liquid container. As a result of the passage of light from the inside of the housing into the liquid container, that is, onto the surface of the liquid, a relatively large illuminated area is obtained, which is increased even more by the reflection of the light from the surface of the liquid. In addition, the liquid container performs its function without the need for any active electrical components.

It is especially advantageous for the direction in which the light proceeds to be essentially toward the bottom plate and/or for at least certain parts of the wall surfaces of the liquid container to be transparent. Directing the light toward the bottom plate ensures that the light entering the liquid container falls on the reflective surface of the liquid, which has the effect of amplifying the signaling effect produced by the light. If at least certain parts of the wall surfaces of the liquid container are transparent, the illumination of the liquid container can be seen from the outside even more easily.

It is also advantageous for the light exit portion and the light entrance portion to be surfaces of complementary shape, which are arranged next to each other with an air gap between them.

It is especially preferred for the light exit portion and the light entrance portion to be arranged at a previously determined angle to the plane of the bottom plate, preferably at an angle ranging from about 20° to about 70°. As a result, the liquid container is illuminated in an especially effective manner.

It is also advantageous for the light exit portion to be designed as a transparent wall portion of the housing or as a window or opening in the housing. The greater the transparency, the better the optical yield for the illumination of the liquid container. In contrast to an opening in the housing, a transparent wall portion and a window both offer the advantage that the structural elements in the interior of the housing are completely enclosed and thus protected.

It is preferable for at least certain parts of the external surface of the light entrance portion to be polished. This prevents the light from being scattered and thus optimizes the light yield.

At the same time, it is advantageous for the internal surface of the light entrance portion to have at least a matte or structured finish. What this achieves is that the light beam, even if it is quite small, is scattered as widely as possible within the liquid container.

It is also advantageous for the light source or light-producing means to comprise one or more light-emitting diodes (LEDs). Alternatively, however, it is also possible to use other types of light sources such as halogen lamps, incandescent lamps, lasers, or other suitable means of illumination. In particular, it is advantageous for the light source to be multicolored; this can be achieved, for example, by the use of a multicolored LED array. This offers the possibility of creating an alarm code, according to which different functional alarms are identified by separate colors.

It is also advantageous for the inside surface of the bottom plate to be polished, which then reflects the incident light more effectively. This leads in turn to a higher light yield during the time that the container is being illuminated.

Also according to the invention is a respiratory humidifier with a housing, a liquid container, and a lighting device as defined above. The respiratory humidifier preferably comprises a control unit, which is able to activate and to deactivate the lighting device. Because the measurement values from sensors or data from other devices connected by electrical interfaces can be evaluated in the control unit, it is logical to activate or to deactivate the lighting device on the basis of these measurements or data values. It is especially advantageous for the control unit to activate the lighting device when a measurement value exceeds or falls below a previously determined reference (or nominal) value. This makes it possible to display the alarms in an optically more conspicuous manner, which is easier for the user to detect. It is also possible to generate acoustic alarm signals in addition to the optical signals.

It is also advantageous for the measurement value to be the liquid level value, a temperature value, or some other type of ventilation signal. This makes it possible to display, for example, an alarm signal originating from a ventilated patient or from the ventilator itself.

The light-producing means or light source can be arranged in a suitable manner on the circuit board(s) of the control unit. This prevents too much space from being occupied. In addition, lighting circuits with integrated light sources such as LEDs are available as integrated components at low cost and are easy to work with.

BRIEF DESCRIPTION OF THE DRAWINGS

The invention is explained below on the basis of a preferred exemplary embodiment with reference to the attached figures:

FIG. 1 shows a perspective view of a housing of a respiratory humidifier with a lighting device according to a preferred embodiment of the present invention;

FIG. 2 shows a perspective view of a respiratory humidifier which comprises a preferred embodiment of the lighting device according to the invention;

FIG. 4 shows a perspective view of a liquid container for a respiratory humidifier according to a preferred embodiment of the present invention; and FIG. 5 shows a perspective cross-sectional view of the liquid container of FIG. 4 from below.

DETAILED DESCRIPTION

Figure 3:
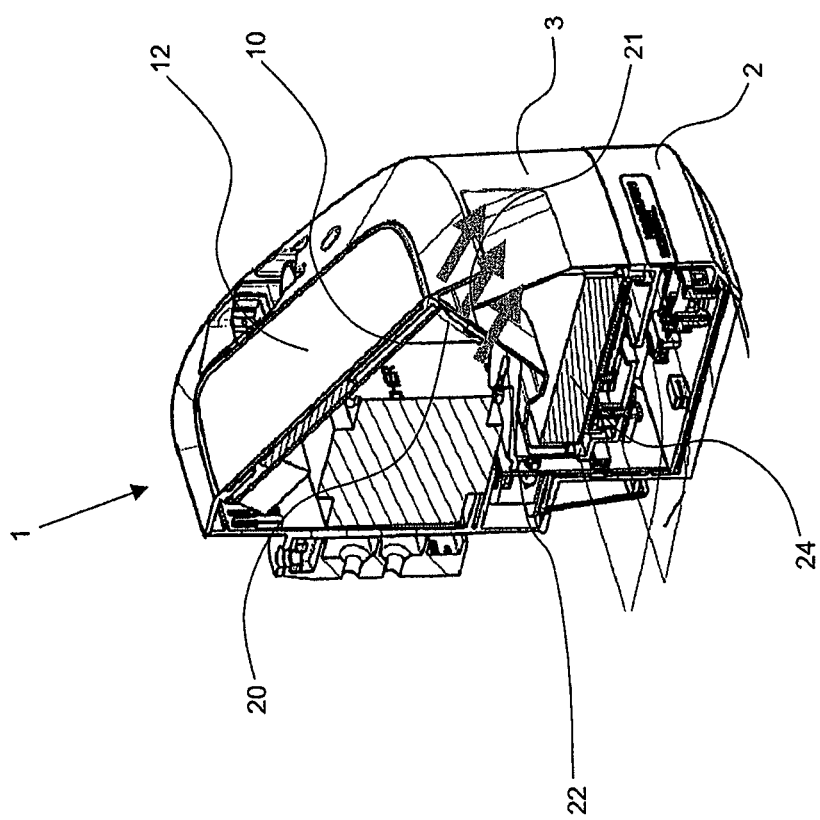
FIG. 3 shows a perspective cross-sectional view of the respiratory humidifier with the preferred embodiment of the lighting device.

FIG. 1 shows a perspective view of the housing 2 of a respiratory humidifier which comprises a lighting device according to a preferred embodiment of the present invention. The housing 2 comprises essentially an L-shape with a horizontal part 4 and a vertical part 6. On the horizontal part 4, a heating plate 8 is arranged, which is oriented essentially horizontally and which covers almost the entire upward-facing surface of the horizontal part 4. A projecting portion 10 extends from approximately the middle of the upper, free end of the vertical part 6, the slanted surface of which portion comprises a user interface 12. The user interface 12 comprises display devices and operating elements 16 (not shown), by means of which, together with a control unit (not shown), the respiratory humidifier can be monitored and controlled. Electrical contact elements 18 are arranged at the upper end of the vertical part 6, offset laterally from the projecting portion 10; these elements can be brought into electrical contact with corresponding connecting parts of a ventilation tubing system. In the area of the projecting portion 10 facing downward toward the horizontal part 4, the housing comprises a portion 14, on the internal surface of which the light source is arranged and from which the light proceeds toward the liquid container to be slid into place.

FIG. 2 shows a perspective diagram of a respiratory humidifier 1 comprising a lighting device according to a preferred embodiment. As can be easily seen in conjunction with FIG. 1, a liquid container 3 has been pushed horizontally onto the housing 2, described in detail on the basis of FIG. 1; the container fits onto the housing 2 in such a way that the respiratory humidifier 1 acquires an essentially continuous lateral surface and an essentially continuous slanted top surface. At the sides, breathing tubes 17 and 19, which are connected by suitable connecting systems to the liquid container 3 and/or to the electric contact elements 18 of the housing 2, project from the upper portion of the liquid container 3. The forward portion of the liquid container 3 comprises a grip 15, which is useful for sliding the liquid container 3 in and out. The dotted line indicates the portion 14 and expresses the fact that, in this area, light from the interior of the housing 2 enters the liquid container 3.

FIG. 3 shows a perspective cross-sectional view of the respiratory humidifier according to FIG. 2, which comprises a preferred embodiment of the inventive lighting device. It is clear from the cross-sectional view that, in the interior of the projecting portion 10, which forms part of the housing 2, a light source or light-producing means 20 is arranged. In the portion which faces downward at a slant toward the bottom plate of the liquid container 3, a light exit portion 22 is formed on the housing 2, through which the light passes on its way to the liquid container 3. In comparison to the surrounding wall thickness, the light exit portion 22 is designed to be a thin housing wall, which is also transparent. This offers the advantage that no additional component made of different material is required. Alternatively, the light exit portion 22 can be designed as a transparent glass or plastic window. The light exit portion 22 can be circular, elliptical, rectangular, or polygonal.

The light entrance portion 21 of the liquid container 3 is arranged immediately adjacent and parallel to the light exit portion 22, the two portions forming a close configuration; through this entrance portion, the light enters the liquid container 3, where it strikes the surface of the liquid 24, by which it is refracted and/or scattered. Because, in the preferred embodiment, the liquid container 3 is made of transparent plastic material, the scattered light reflected from the surface of the liquid is distributed over a large part of the interior space of the liquid container 3 and is therefore visible not only from the outside, that is, from the front, but also from the sides of the liquid container 3.

FIG. 4 shows a perspective view of the liquid container 3 essentially from above, so that the light entrance portion 21 can be seen from above. At least certain parts of the external surface of the light entrance portion are polished. The polished surface is intended to have the effect of minimizing the amount of light which is scattered by this surface, as a result of which as much light as possible penetrates directly into the liquid container 3. As an alternative, it is possible to cover the light entrance portion 21 with a plastic sheet or to provide it with a coating of appropriate color, so that the same effect is achieved. The larger the light entrance portion 21, the greater the amount of light entering the liquid container 3, which in turn increases the signaling effect of the inventive lighting device.

FIG. 5 shows a perspective cross-sectional view of the internal surface 23 of the light entrance portion of the liquid container 3. In contrast to the external surface 21, the internal surface 23 of the light entrance portion has a matte or structured finish. This has the effect of scattering the light over the widest possible area inside the liquid container 3. Here, too, it is possible to achieve the same effect by other means, such as by applying a plastic sheet or by spraying on a suitable coating material.

Overall, what is obtained in the preferred embodiment of the present invention illustrated in the figures is a very good optical signal source for alarms, which is visible from several sides of the respiratory humidifier. The lighting device makes use of the fact that the water is also illuminated, which then reflects the light and thus contributes to the illumination of the entire liquid container 3 from the inside. In certain cases, the bottom plate of the liquid container can also be designed to be highly reflective, i.e., polished, as a result of which the lighting effect is intensified even more.

With the subject matter of the present invention, a lighting device for a respiratory humidifier has been provided, which can signal an alarm state optically in highly visible fashion in many different directions and which can be realized with a simple, low-cost design and structure.

The invention claimed is:

1. A respiratory humidifier with a lighting device to facilitate observation of the fill level of water in a liquid container from which humidity is added to the breathing gas, the humidifier including a housing with a heating plate and the liquid container with a bottom plate which, when brought into contact with the heating plate, heats the liquid in the liquid container, wherein:
   the housing includes a projecting portion having a downwardly-facing wall surface with a light-exit portion, the housing containing an electrical light source directed toward the light-exit portion such that light from the electrical light source exits downwardly therefrom;
   the liquid container includes an upwardly-facing light-entrance portion directly adjacent to and facing the light-exit portion and positioned above the water therein such that light proceeds from the light source through the light-exit portion and light-entrance portion downwardly into the liquid container to illuminate the surface of the water, and at least certain parts of the container surfaces of the liquid container being transparent.

2. The respiratory humidifier of claim 1 wherein the light-exit portion and the light-entrance portion are flat.

3. The respiratory humidifier of claim 2 wherein the light-exit portion and the light-entrance portion are arranged at an angle of from about 20° to about 70° to the plane of the bottom plate.

4. The respiratory humidifier of claim 1 wherein the light-exit portion and the light-entrance portion comprise surfaces of complementary shape and defining an air gap therebetween.

5. The respiratory humidifier of claim 4 wherein the light-exit portion and the light-entrance portion are flat.

6. The respiratory humidifier of claim 5 wherein the light-exit portion and the light-entrance portion are arranged at an angle of from about 20° to about 70° to the plane of the bottom plate.

7. The respiratory humidifier of claim 1 wherein at least portions of the external surface of the light-entrance portion are polished.

8. The respiratory humidifier of claim 1 wherein at least certain portions of the internal surface of the light-entrance portion have a matte or structured finish.

9. The respiratory humidifier of claim 1 wherein the light source is multicolored.

10. The respiratory humidifier of claim 1 wherein the light source comprises one or more light-emitting diodes (LEDs).

11. The respiratory humidifier of claim 10 wherein the light source is multicolored.

12. The respiratory humidifier of claim 1 wherein the inside surface of the bottom plate is polished.

13. The respiratory humidifier of claim 1 further comprising a control unit adapted for activating and deactivating the lighting device.

14. The respiratory humidifier of claim 13 wherein the control unit is adapted to activate the lighting device when a measurement value exceeds or falls below a previously-determined reference value.

15. The respiratory humidifier of claim 14 wherein the measurement value is a fill-level value or a temperature value.

16. The respiratory humidifier of claim 5 wherein the light-exit portion and light-entrance portion are substantially parallel.

* * * * *